United States Patent
Hailes et al.

(10) Patent No.: US 11,098,006 B2
(45) Date of Patent: Aug. 24, 2021

(54) LIPIDS AND COMPLEXES FOR THE DELIVERY OF BIOLOGICALLY-ACTIVE MATERIAL TO CELLS

(71) Applicant: RYBOQUIN COMPANY LTD, London (GB)

(72) Inventors: Helen Claire Hailes, London (GB); Alethea Bernice Tabor, London (GB); Mohn Firouz Mohd Mustapa, London (GB); Stephen Lewis Hart, London (GB); Aristides Tagalakis, London (GB)

(73) Assignee: RYBOQUIN COMPANY LTD, London (GB)

( * ) Notice: Subject to any disclaimer, the term of this patent is extended or adjusted under 35 U.S.C. 154(b) by 192 days.

(21) Appl. No.: 16/082,785

(22) PCT Filed: Mar. 10, 2017

(86) PCT No.: PCT/GB2017/050664
§ 371 (c)(1),
(2) Date: Sep. 6, 2018

(87) PCT Pub. No.: WO2017/153779
PCT Pub. Date: Sep. 14, 2017

(65) Prior Publication Data
US 2019/0084923 A1     Mar. 21, 2019

(30) Foreign Application Priority Data

Mar. 11, 2016  (GB) ...................... 1604235

(51) Int. Cl.
*C07C 217/28*     (2006.01)
*A61K 47/54*      (2017.01)
*A61P 35/00*      (2006.01)

(52) U.S. Cl.
CPC .......... *C07C 217/28* (2013.01); *A61K 47/543* (2017.08); *A61P 35/00* (2018.01)

(58) Field of Classification Search
CPC .......................... C07C 217/28; A61K 47/543
See application file for complete search history.

(56) References Cited

U.S. PATENT DOCUMENTS 6,083,741 A   7/2000  Hart et al.
6,458,026 B1  10/2002 Hart
(Continued)

FOREIGN PATENT DOCUMENTS

DE   1003898   8/2005
DE   1368371   10/2008
(Continued)

OTHER PUBLICATIONS

Bennett et al. 1995. "A Flexible Approach to Synthetic Lipid Ammonium Salts for Polynucleotide Transfection." Tetrahedron Letters, vol. 36, No. 13, pp. 2017-2210.
(Continued)

*Primary Examiner* — Yate' K Cutliff
(74) *Attorney, Agent, or Firm* — David S. Bradin; Nexsen Pruet, LLC (57) ABSTRACT

A lipid comprising a tri-chain cation having a cationic head group and three or more $C_{7-24}$ hydrocarbyl groups for use in non-viral gene delivery systems, for example in the formation of lipopolyplex transfection vectors. Exceptionally good nucleic acid transfection is observed when nucleic acid and targeting peptides are formulated with the lipid of the invention (or lipid formulated with a co-lipid) into a LPD complex.

13 Claims, 3 Drawing Sheets

(56) References Cited

U.S. PATENT DOCUMENTS

| | | |
|---|---|---|
| 7,256,043 B2 | 8/2007 | Hart et al. |
| 7,598,421 B2 | 10/2009 | Hailes et al. |
| 7,704,969 B2 | 4/2010 | Hart et al. |
| 7,820,624 B2 | 10/2010 | Hart et al. |
| 8,026,341 B2 | 9/2011 | Hart et al. |
| 9,399,016 B2 * | 7/2016 | Hart .................... A61K 9/1271 |

FOREIGN PATENT DOCUMENTS

| | | |
|---|---|---|
| DE | 0792166 | 3/2011 |
| DE | 1964849 | 10/2011 |
| DE | 2035566 | 8/2013 |
| FR | 1003898 | 8/2005 |
| FR | 1368371 | 10/2008 |
| FR | 0792166 | 3/2011 |
| FR | 1964849 | 10/2011 |
| FR | 2035566 | 8/2013 |
| GB | 1003898 | 8/2005 |
| GB | 1368371 | 10/2008 |
| GB | 0792166 | 3/2011 |
| GB | 1964849 | 10/2011 |
| GB | 2035566 | 8/2013 |
| WO | 2007138324 | 12/2007 |

OTHER PUBLICATIONS

Hurley et al. 2008. "Mono- and dicationic short PEG and methylene dioxyalkylglycerols for use in synthetic gene delivery systems." Org. Biomol. Chem., vol. 6, pp. 2554-2559.

* cited by examiner

LIPIDS AND COMPLEXES FOR THE DELIVERY OF BIOLOGICALLY-ACTIVE MATERIAL TO CELLS

FIELD OF THE INVENTION

The present invention relates to lipid derivatives suitable for delivery of biologically-active materials, for example nucleic acids, proteins or small molecules, to a cell. The invention further relates to complexes for use in the preparation of non-viral vectors for the delivery of biologically-active material to cells that include such lipids, for example, in combination with peptides and the use of such complexes, for example in prophylaxis, treatment and vaccination, or an in vitro laboratory setting.

BACKGROUND TO THE INVENTION

Gene delivery for therapy or other purposes is well-known, particularly for the treatment of diseases such as cystic fibrosis and certain cancers. The term refers to the delivery into a cell of a gene or part of a gene to correct some deficiency. In the present specification the term is used also to refer to any introduction of nucleic acid material into target cells, and includes gene vaccination and the in vitro production of commercially-useful proteins in so-called cell factories.

Cell delivery systems fall into three broad classes, namely those that involve direct injection of naked DNA or RNA, those that make use of viruses or genetically modified viruses and those that make use of non-viral delivery agents. Each has its advantages and disadvantages. Although viruses as delivery agents have the advantages of high efficiency and high cell selectivity, they have the disadvantages of toxicity, production of inflammatory responses and difficulty in dealing with large DNA fragments.

Non-viral gene delivery systems are based on the compaction of genetic material into nanometric particles by electrostatic interaction between the negatively charged phosphate backbone of DNA or RNA and cationic lipids, peptides or other polymers (Erbacher, P. et al, *Gene Therapy*, 1999, 6, 138-145). The use of non-viral transfection vectors that include lipids, as opposed to viruses, can result in lower toxicity, especially lower immunogenicity; greater safety; reduced cost, reasonably efficient targeting, and an enhanced packaging ability, e.g. the ability to deal with large fragments of nucleic acid material. Unfortunately, lower transfection efficiencies have been noted. Non-viral gene therapy vectors have been the subject of recent reviews: (Yin H, Kanasty R L, Eltoukhy A A, Vegas A J, Dorkin J R, Anderson D G. *Non-viral vectors for gene-based therapy.* Nature reviews Genetics. 2014; 15:541-55; Schroeder A, Levins C G, Cortez C, Langer R, Anderson D G. *Lipid-based nano-therapeutics for siRNA delivery.* J Intern Med. 2010; 267: 9-21; Zhao Y, Huang L. *Lipid nanoparticles for gene delivery.* Adv Genet. 2014; 88:13-36.

Known complexes for gene delivery include lipoplex for lipid based nucleic acid complexes, polyplex for peptide or polymer-based complexes and lipopolyplex for hybrid systems (Felgner et al., Human Gene Therapy 8, 1997, 511-512). As used herein, the term "LPD" is a form of lipopolyplex representing a formulation comprising a lipid, an integrin- (or other receptor-) binding peptide and DNA (or other nucleic acid). LPD complexes achieve transfection via an integrin-mediated or other receptor-mediated pathway; they do not necessarily need to have an overall positive charge so undesirable serum interaction can be reduced. The peptide component provides a nucleic acid packaging function, shielding the DNA or RNA from intracellular or extracellular degradation, endosomal or otherwise. The lipid components mediate interactions with endosomal lipid bilayers by membrane fusion or permeabilisation, reducing endosomal or lysosomal degradation and allowing trafficking of the nucleic acid cargo the cytoplasm. The peptide component can be designed to be cell-type specific or cell-surface receptor specific. For example the degree of specificity for integrin or other receptors can confer a degree of cell specificity to the LPD complex. Specificity results from the targeting to the cell-surface receptors (for example integrin receptors), and transfection efficiencies comparable to some adenoviral vectors can be achieved. (Du Z, Munye M M, Tagalakis A D, Manunta M D, Hart S L. *The role of the helper lipid on the DNA transfection efficiency of lipopolyplex formulations.* Sci Rep. 2014; 4:7107; Welser K, Campbell F, Kudsiova L, Mohammadi A, Dawson N, Hart S L, et al. *Gene delivery using ternary lipopolyplexes incorporating branched cationic peptides: the role of Peptide sequence and branching.* Mol Pharm. 2013; 10:127-41; Meng Q H, Irvine S, Tagalakis A D, McAnulty R J, McEwan J R, Hart S L. *Inhibition of neointimal hyperplasia in a rabbit vein graft model following non-viral transfection with human iNOS cDNA.* Gene Ther. 2013; 20:979-86; Manunta M D, McAnulty R J, McDowell A, Jin J, Ridout D, Fleming J, et al. *Airway deposition of nebulized gene delivery nanocomplexes monitored by radioimaging agents.* Am J Respir Cell Mol Biol. 2013; 49:471-80; Kenny G D, Bienemann A S, Tagalakis A D, Pugh J A, Welser K, Campbell F, et al. *Multifunctional receptor-targeted nanocomplexes for the delivery of therapeutic nucleic acids to the Brain.* Biomaterials. 2013; 34:9190-200; Tagalakis A D, He L, Saraiva L, Gustafsson K T, Hart S L. *Receptor-targeted liposome-peptide nanocomplexes for siRNA delivery.* Biomaterials. 2011; 32:6302-15; Tagalakis A D, Grosse S M, Meng Q H, Mustapa M F, Kwok A, Salehi S E, et al. *Integrin-targeted nanocomplexes for tumour specific delivery and therapy by systemic administration.* Biomaterials. 2011; 32:1370-6; Manunta M D, McAnulty R J, Tagalakis A D, Bottoms S E, Campbell F, Hailes H C, et al. *Nebulisation of receptor-targeted nanocomplexes for gene delivery to the airway epithelium.* PLoS One. 2011; 6:e26768; Grosse S M, Tagalakis A D, Mustapa M F, Elbs M, Meng Q H, Mohammadi A, et al. *Tumor-specific gene transfer with receptor-mediated nanocomplexes modified by polyethylene glycol shielding and endosomally cleavable lipid and peptide linkers.* FASEB J. 2010; 24:2301-13.

Peptides that target human airway epithelial cells have been reported (WO02/072616). Peptides that target dendritic cells have been reported (WO2004/108938).

Lipid/peptide vectors transfect a range of cell lines and primary cell cultures with high efficiency and low toxicity: epithelial cells (40% efficiency), vascular smooth muscle cells (50% efficiency), endothelial cells (30% efficiency) and haematopoietic cells (10% efficiency). Furthermore, in vivo transfection of bronchial epithelium of mouse has been demonstrated (Manunta M D, McAnulty R J, Tagalakis A D, Bottoms S E, Campbell F, Hailes H C, et al. *Nebulisation of receptor-targeted nanocomplexes for gene delivery to the airway epithelium.* PLoS One. 2011; 6:e26768; Tagalakis A D, McAnulty R J, Devaney J, Bottoms S E, Wong J B, Elbs M, et al. *A receptor-targeted nanocomplex vector system optimized for respiratory gene transfer.* Mol Ther. 2008; 16:907-15. Jenkins et al., *Formation of LID vector complexes in water alters physicochemical properties and enhances pulmonary gene expression in vivo*, Gene Therapy

2003, 10, 1026-34), rat lung (Jenkins et al., *An integrin-targeted non-viral vector for pulmonary gene therapy*, Gene Therapy 2000, 7, 393-400) and pig lung (Manunta M D, McAnulty R J, McDowell A, Jin J, Ridout D, Fleming J, et al. *Airway deposition of nebulized gene delivery nanocomplexes monitored by radioimaging agents*. Am J Respir Cell Mol Biol. 2013; 49:471-80; Cunningham et al., *Evaluation of a porcine model for pulmonary gene transfer using a novel synthetic vector*, J Gene Med 2002, 4, 438-46) and with efficiency comparable to that of an adenoviral vector (Jenkins et al., 2000, as above).

A peptide for use in such LPD complexes or lipid/peptide complexes must have two functionalities: a "head group" containing a cell surface receptor—(for example integrin) recognition sequence and a "tail" that can bind DNA non-covalently. Known peptides in which these two components are covalently linked via a spacer in a way that does not interfere with their individual functions include peptides in which the "tail" is a polycationic nucleic acid-binding component, such as peptide 6 as described in WO96/15811.

Initial experiments involving LPD complexes including such peptides have indicated insufficiently high transfection properties by the systemic, or intravenous, route of delivery. The likely problem, as described for other polycationic vectors is association of the vector with serum proteins and red cell membranes leading to poor solubility and rapid clearance of the vector by the reticuloendothelial systems (Dash, P. R., Read, M. L., Barrett, L. B., Wolfert, M. A., Seymour, L. W. (1999) *Gene Therapy* 6, 643-50). Vectors that have displayed some transfection activity by systemic administration have been effective largely in first-pass capillary beds of organs such as the liver and lung (Fenske, D. B., MacLachlan, I., Cullis, P. R. (2001). *Curr Opin Mol Ther* 3, 153-8). While such non-specific transfection activity may have some therapeutic applications, safe clinical use for specific applications demands vectors with far greater target specificity.

Regarding the lipid component of the LPD complexes, cationic lipids for such a use were developed by Felgner in the late 1980s, and reported in Proc. Natl. Acad. Sci. USA 84, 7413-7417, 1987 and in U.S. Pat. No. 5,264,618. Felgner developed the now commercially-available cationic liposome known by the trademark "Lipofectin" which consists of the cytofectin, DOTMA 1 and the neutral lipid DOPE 2 in a 1:1 ratio.

Various other cationic liposome formulations have since been devised, most of which combine a synthetic cationic cytofectin and a neutral lipid. Some, for example, are based on the glycerol-skeleton (such as DOTMA) or on cholesterol, such as DC-Chol 3.

DC-Chol 3

The aim in developing new cytofectins has often been to optimise the delivery properties of the resulting vector for a wide variety of cell types, and for in vivo applications.

Cytofectins and other cationic lipids are positively charged molecules having a cationic head group attached via some spacer to a hydrophobic tail. In addition to the DOTMA 1 analogues, a range of analogues with either ether or ester linkages to the glycerol skeleton, alternative alkyl chain groups and functionalised head groups have been reported, such as the diester DOTAP 4. A review of these materials, and of the mechanisms by which they operate, may be found in Angew. Chem. Int. Ed. 37, 1768-1785, 1998. A common feature of many known DOTMA 1 analogue cyclofectins is the presence of two hydrophobic tails attached to the cationic head group.

Studies have established that for many cell types, in vitro experiments with DOTMA 1 and DOTAP 4 gave comparable levels of transfection, but when used in vivo DOTMA 1 exhibited higher transfection activities. Other analogues reported include the diester DORI 5 with an N,N-dimethyl N-ethanolamine head group, the corresponding diether DORIE 6, and C14:0 analogue DIMRIE 7.

DOTMA 1

DOPE 2

DOTAP 4 (R = Me)
DORI 5 (R = CH$_2$CH$_2$OH)

Y = OH, R' = oleyl, DORIE 6
Y = OH, R' = C$_{14}$H$_{29}$, DMRIE 7
Y = NH$_2$, R' = C$_{14}$H$_{29}$, βAE-DMRIE 8

Cytofectins containing such quaternary amine hydroxyalkyl moieties have proven particularly interesting, and lipids with shorter hydroxyalkyl groups gave rise to improved properties. For example, co-formulation of DORIE 6, with a hydroxyethyl moiety at the headgroup with the helper lipid DOPE 2, gave higher transfection efficacies in COS.7 cells, compared to lipids with hydroxypropyl-hydroxypentyl groups. All these hydroxyalkyl cytofectins were more active than DOTMA 1 and DMRIE 7 was also highlighted as one of the more efficient lipids.

Cytofectins with terminal hydroxyl groups were believed to be particularly effective, either because the hydroxyl group was able to increase the liposome interaction with DNA or cellular membranes, or because it was able to stabilise the cationic lipid:DOPE 2 bilayer structure, through charge neutralisation and/or hydrogen bonding.

WO 2005/117985 describes lipids comprising one or more polyethylene glycol (PEG) groups (i.e. PEGylated lipids) and shows that such PEGylated lipids display benefits over lipids without PEG groups (i.e. non-PEGylated lipids). In particular, the problem of rapid clearance of lipids by the reticuloendothelial system caused by their binding to plasma proteins and vector aggregation may be ameliorated by shielding the vectors with polymeric PEG moieties. However, PEGylation often leads to greatly reduced transfection efficiency, and there remains a need for lipids which are not rapidly cleared by the reticuloendothelial system, but display satisfactory transfection efficiency.

The lipid, DODEG4 13, a glycerol-based diether lipid possessing a short n-ethylene glycol headgroup and its application in lipopolyplex (lipid-peptide-DNA) targeted delivery has previously been reported in Hurley, C. A.; Wong, J. B.; Ho, J.; Writer, M.; Irvine, S. A.; Lawrence, M. J.; Hart, S. L.; Tabor, A. B.; Hailes, H. C. *Org. Biomol. Chem.* 2008, 6, 2554-2559 and in Welser, K.; Campbell, F.; Kudsiova, L.; Mohammadi, A.; Dawson, N.; Hart, S. L.; Barlow, D. J.; Hailes, H. C.; Lawrence, M. J.; Tabor, A. B.; *Mol. Pharm.* 2013, 10, 127-141.

SUMMARY OF THE INVENTION

The present inventors have discovered a new class of ionic compounds that are useful as, or as a component of, the lipid part of an LPD complex. The ionic compounds are tri-chain cationic lipids that have three hydrophobic tails attached to the cationic head group, one of which being attached via an alkylene glycol linkage. It has been found that the novel tri-chain lipids improve the transfection efficiency of synthetic transfection vectors into which they are incorporated, for example, compared to known di-chain DOTMA 1 analogue cytofectins which include two hydrophobic tails attached to the cationic head group.

In a first aspect, the present invention provides an ionic compound of formula (Ia):

wherein:
Each of X and Y are the same or different and is selected from —O—, and —O—C(O)— where the carbonyl carbon is bonded to group R$^1$ or R$^2$ R$^1$ and R$^2$ are the same or different and are each independently selected from a C$_{12-24}$ hydrocarbyl group which is unsubstituted or substituted by one or more substituents selected from hydroxy, halogen and OR$^A$, wherein R$^A$ is a C$_{1-6}$ hydrocarbyl group;

R$^3$ and R$^4$ are the same or different and are each independently selected from a C$_{1-10}$ hydrocarbyl group which is unsubstituted or substituted by one or more substituents selected from hydroxy, halogen, —OR', —C(O)OH, —CN, —N(R')$_2$, and —C(O)R', wherein each R' is the same or different and is a C$_{1-6}$ hydrocarbyl group;

Sp and W are together a bond; or
Sp is a C$_{1-8}$ alkylene group which is unsubstituted or substituted by one or more substituents selected from hydroxy, halogen and OR', wherein R' is a C$_{1-6}$ hydrocarbyl group; and W is selected from bond, —O—C(O)—, —C(O)—O— and —O—;

each B is the same or different and is a C$_{1-6}$ alkylene group which is unsubstituted or substituted by one or more substituents selected from hydroxy, halogen, —OR$^A$, —N$^A$R$^A$ and —OC(O)R$^A$;

wherein each R$^A$ is independently selected from C$_{1-4}$ hydrocarbyl;

m is an integer from 1 to 8; and
Q is selected from —OR and —O—C(O)—R$^5$, wherein R$^5$ is selected from a C$_{7-24}$ hydrocarbyl group which is unsubstituted or substituted by one or more substituents selected from hydroxy, halogen and OR$^A$, wherein R$^A$ is a C$_{1-6}$ hydrocarbyl group.

In a second aspect, the invention provides a transfection complex that comprises (i) an ionic compound of the first aspect of the invention. Advantageously, the transfection complex of the second aspect of the invention further comprises (iv) a nucleic acid or other active compound for delivery to a cell. Advantageously, the transfection complex of the second aspect of the invention is suitable for use as a medicament or a vaccine.

In a third aspect, the invention provides a pharmaceutical composition which comprises the ionic compound of the first aspect of the invention or the transfection complex of the second aspect of the invention in admixture or conjunction with a pharmaceutically suitable carrier.

In a fourth aspect, the invention provides an ionic compound of the first aspect of the invention or a transfection complex of the second aspect of the invention for use in therapy.

In a fifth aspect, the invention provides a method for the treatment or prophylaxis of a condition caused in a human or in a non-human animal by a defect and/or a deficiency in a gene or for therapeutic or prophylactic immunisation, or for anti-sense or RNAi therapy, which comprises administering the ionic compound of the first aspect of the invention or the transfection complex of the second aspect of the invention to the human or to the non-human animal.

In a sixth aspect, the invention provides a method for the treatment of a human or non-human animal suffering from a cancer which comprises administering the ionic compound of the first aspect of the invention or the transfection complex of the second aspect of the invention to the human or to the non-human animal.

In a seventh aspect, the invention provides the use of the ionic compound of the first aspect of the invention or the transfection complex of the second aspect of the invention for the manufacture of a medicament for the treatment or prophylaxis of a condition caused in a human or a non-human animal by a defect and/or a deficiency in a gene, or for therapeutic or prophylactic immunisation, or for anti-sense or RNAi therapy.

In an eighth aspect, the invention provides the use of the ionic compound of the first aspect of the invention or the transfection complex of the second aspect of the invention for the manufacture of a medicament for the treatment or prophylaxis of cancer in a human or a non-human animal.

In a ninth aspect, the invention provides the ionic compound of the first aspect of the invention or the transfection complex of the second aspect of the invention for use in the treatment or prophylaxis of a condition caused in a human or a non-human animal by a defect and/or a deficiency in a gene, or for therapeutic or prophylactic immunisation, or for anti-sense or RNAi therapy.

In a tenth aspect, the invention provides the ionic compound of the first aspect of the invention or the transfection complex of the second aspect of the invention for use in the treatment or prophylaxis of cancer in a human or a non-human animal.

In an eleventh aspect, the invention provides a kit that comprises:
  (i) an ionic compound of the first aspect of the invention nucleic acid;
  a peptide comprising (ii) a polycationic nucleic acid-binding component and (iii)
  a cell surface receptor binding component; and, optionally, (iv) a nucleic acid.

It was found that the transfection efficacies of LPD (lipid-peptide-nucleic acid) lipopolyplexes comprising the tri-chain lipids of the invention were significantly higher than for the di-chain analogues. We have shown previously that lipid components of LPD complexes are particularly important for intracellular trafficking across the endosomal membrane and so it is hypothesised that these lipids enhance transfection efficiency by contributing to that process (Du Z, Munye M M, Tagalakis A D, Manunta M D, Hart S L. *The role of the helper lipid on the DNA transfection efficiency of lipopolyplex formulations*. Sci Rep. 2014; 4:7107). They may also affect the internal structure of the nanocomplex enabling more efficient release of the nucleic acid within the cell (Munye M M, Ravi J, Tagalakis A D, McCarthy D, Ryadnov M G, Hart S L. *Role of liposome and peptide in the synergistic enhancement of transfection with a lipopolyplex vector*. Sci Rep. 2015; 5:9292). The novel tri-chain lipids of the invention thus provide a new generation of effective cytofectin gene delivery vectors, based on the use of three hydrophobic chains.

DETAILED DESCRIPTION OF THE INVENTION

Lipids

In a first aspect, the present invention provides an ionic compound of formula (Ia):

(Ia)

wherein:
Each of X and Y are the same or different and is selected from —O—, and —O—C(O)— where the carbonyl carbon is bonded to group $R^1$ or $R^2$ $R^1$ and $R^2$ are the same or different and are each independently selected from a $C_{12-24}$ hydrocarbyl group which is unsubstituted or substituted by one or more substituents selected from hydroxy, halogen and $OR^A$, wherein $R^A$ is a $C_{1-6}$ hydrocarbyl group;

$R^3$ and $R^4$ are the same or different and are each independently selected from a $C_{1-10}$ hydrocarbyl group which is unsubstituted or substituted by one or more substituents selected from hydroxy, halogen, —OR', —C(O)OH, —CN, —N(R')$_2$, and —C(O)R', wherein each R' is the same or different and is a $C_{1-6}$ hydrocarbyl group;

Sp and W are together a bond; or

Sp is a $C_{1-8}$ alkylene group which is unsubstituted or substituted by one or more substituents selected from hydroxy, halogen and OR', wherein R' is a $C_{1-6}$ hydrocarbyl group; and W is selected from bond, —O—C(O)—, —C(O)—O— and —O—;

each B is the same or different and is a $C_{1-6}$ alkylene group which is unsubstituted or substituted by one or more substituents selected from hydroxy, halogen, —OR$^A$, —NR$^A$R$^A$ and —OC(O)R$^A$;

wherein each R$^A$ is independently selected from $C_{1-4}$ hydrocarbyl;

m is an integer from 1 to 8; and

Q is selected from —OR$^5$ and —O—C(O)—R$^5$, wherein R$^5$ is selected from a $C_{12-24}$ hydrocarbyl group which is unsubstituted or substituted by one or more substituents selected from hydroxy, halogen and OR$^A$, wherein R$^A$ is a $C_{1-6}$ hydrocarbyl group.

Optionally, the ionic compound of the first aspect of the invention is of the formula (Ia) wherein either Sp and W are both bond, or Sp is an unsubstituted $C_{1-8}$ alkylene group and W is bond, —O—C(O)—, —C(O)—O— or —O—, especially bond, —C(O)—O— or —O—. Advantageously, Sp and W are both bond, or Sp is an unsubstituted $C_{1-8}$ alkylene group and W is —C(O)—O—.

The term "alkylene" as used herein refers to a divalent radical derived from removing two hydrogen atoms from an alkane, also known as an alkanediyl group, for example, —CH(CH$_3$)CH$_2$-(propane-1,2-diyl).

The term "hydrocarbyl" as used herein refers to a univalent group formed by removing a hydrogen atom from a hydrocarbon, for example, ethyl or phenyl.

The ionic compound of the first aspect of the invention is optionally of formula (b):

(Ib)

wherein:
Each of X and Y are the same or different and is selected from —O—, and —O—C(O)— where the carbonyl carbon is bonded to group $R^1$ or $R^2$ $R^1$ and $R^2$ are the same or different and are each independently selected from a $C_{12-24}$ hydrocarbyl group which is unsubstituted or substituted by one or more substituents selected from hydroxy, halogen and OR$^A$, wherein R$^A$ is a $C_{1-6}$ hydrocarbyl group;

$R^3$ and $R^4$ are the same or different and are each independently selected from a $C_{1-10}$ hydrocarbyl group which is unsubstituted or substituted by one or more substituents selected from hydroxy, halogen, —OR', —C(O)OH, —CN, —N(R')$_2$, and —C(O)R', wherein each R' is the same or different and is a $C_{1-6}$ hydrocarbyl group;

each B is the same or different and is a $C_{1-6}$ alkylene group which is unsubstituted or substituted by one or more substituents selected from hydroxy, halogen, —OR$^A$, —NR$^A$R$^A$ and —OC(O)R$^A$, and is preferably unsubstituted; wherein each R$^A$ is independently selected from $C_{1-4}$ hydrocarbyl;

m is an integer from 1 to 8; and

Q is selected from —OR and —O—C(O)—R$^5$, $C_{12-24}$ hydrocarbyl group which is unsubstituted or substituted by one or more substituents selected from hydroxy, halogen and OR$^A$, wherein R$^A$ is a $C_{1-6}$ hydrocarbyl group.

Optionally, the ionic compound of the first aspect of the invention is of the formula (Ta) or (Ib), wherein each B is selected from an unsubstituted $C_{1-3}$alkylene group, especially ethylene.

The ionic compound of the first aspect of the invention is optionally of formula (Ic):

(Ic)

wherein:
Each of X and Y are the same or different and is selected from —O—, and —O—C(O)— where the carbonyl carbon is bonded to group $R^1$ or $R^2$ $R^1$ and $R^2$ are the same or different and are each independently selected from a $C_{12-24}$ hydrocarbyl group which is unsubstituted or substituted by one or more substituents selected from hydroxy, halogen and OR$^A$, wherein R$^A$ is a $C_{1-6}$ hydrocarbyl group;

$R^3$ and $R^4$ are the same or different and are each independently selected from a $C_{1-10}$ hydrocarbyl group which is unsubstituted or substituted by one or more substituents selected from hydroxy, halogen, —OR', —C(O)OH, —CN, —N(R')$_2$, and —C(O)R', wherein each R' is the same or different and is a $C_{1-6}$ hydrocarbyl group;

m is an integer from 1 to 8; and

Q is selected from —OR and —O—C(O)—R$^5$, wherein R$^5$ is selected from a $C_{12-24}$ hydrocarbyl group which is unsubstituted or substituted by one or more substituents selected from hydroxy, halogen and OR$^A$, wherein R$^A$ is a $C_{1-6}$ hydrocarbyl group.

The term "hydrocarbyl" as used herein refers to straight or branched, saturated or unsaturated groups unless otherwise specified.

Optionally, the ionic compound of the first aspect of the invention is of the formula (Ia), (Ib) or (Ic), wherein $R^1$ and $R^2$ are the same or different and are each independently a $C_{14-22}$ hydrocarbyl group, for example, an unsaturated $C_{14-22}$ alkenyl group having one, two or three double bonds, especially on double bond. Advantageously, $R^1$ and $R^2$ are the same or different and are each independently a straight chain, unsaturated $C_{16}$ or $C_{18}$ alkenyl group having one double bond. Optionally $R^1$ and $R^2$ are selected from —$(CH_2)_{5-10}CH$=$CH(CH_2)_{5-9}CH_3$, especially —$(CH_2)_{6-9}CH$=$CH(CH_2)_{6-8}CH_3$, such as —$(CH_2)_7CH$=$CH(CH_2)_7CH_3$ or —$(CH_2)_8CH$=$CH(CH_2)_7CH_3$. Preferably, the double bond is cis and $R^1$ and $R^2$ are selected from —$(CH_2)_{5-10}CH[Z]$=$CH(CH_2)_{5-9}CH_3$, especially —$(CH_2)_{6-9}CH[Z]$=$CH(CH_2)_{6-8}$—$CH_3$, such as —$(CH_2)_7CH[Z]$=$CH(CH_2)_7CH_3$ or —$(CH_2)_8CH[Z]$=$CH(CH_2)_7CH_3$. Preferably, X—$R^1$ and Y—$R^2$ are selected from —O—$(CH_2)_8CH[Z]$=$CH(CH_2)_7CH_3$ and —O—C(O)—$(CH_2)_7CH[Z]$=$CH(CH_2)_7CH_3$. Preferably, each of X and Y are the same. Preferably, each of $R^1$ and $R^2$ are the same. Preferably, each of X—$R^1$ and Y—$R^2$ are the same. Preferably, each of X—$R^1$ and Y—$R^2$ are the same and are selected from —O—$(CH_2)_8CH[Z]$=$CH(CH_2)_7CH_3$ and —O—C(O)—$(CH_2)_7CH[Z]$=$CH(CH_2)_7CH_3$.

Optionally, the ionic compound of the first aspect of the invention is of the formula (Ia), (Ib) or (Ic), wherein $R^3$ and $R^4$ are the same or different and are each independently selected from a straight or branched, unsubstituted $C_{1-10}$ alkyl group, for example, a straight or branched, unsubstituted $C_{1-6}$ alkyl group, especially a straight or branched, unsubstituted $C_{1-4}$ alkyl group, such as methyl or ethyl. Advantageously, $R^3$ and $R^4$ are both the same, for example, both methyl or both ethyl, especially both methyl.

Optionally, the ionic compound of the first aspect of the invention is of the formula (Ia), (Ib) or (Ic), wherein m is selected from 1, 2, 3, 4, 5, 6 or 7, for example 2, 3, 4, 5 or 6, especially 2, 3, 4 or 5. In a further embodiment of the first aspect of the invention, m is 3 or 4.

Optionally, the ionic compound of the first aspect of the invention is of the formula (Ia), (Ib) or (Ic), wherein Q is selected from —$OR^5$ and —O—C(O)—$R^5$ and $R^5$ is selected from a $C_{12-24}$ hydrocarbyl group, such as a $C_{14-22}$ hydrocarbyl group, for example, an unsaturated $C_{14-22}$ alkenyl group having one, two or three double bonds, especially a straight chain, unsaturated $C_{16}$ or $C_{18}$ alkenyl group having one double bond, especially a cis double bond. Optionally $R^5$ is —$(CH_2)_{5-10}CH$=$CH(CH_2)_{5-9}CH_3$, especially —$(CH_2)_{6-9}CH$=$CH(CH_2)_{6-8}CH_3$, such as —$(CH_2)_7CH$=$CH(CH_2)_7CH_3$ or —$(CH_2)_8CH$=$CH(CH_2)_7CH_3$. Preferably the double bond is cis and $R^5$ is —$(CH_2)_{5-10}CH[Z]$=$CH(CH_2)_{5-9}CH_3$, especially —$(CH_2)_{6-9}CH[Z]$=$CH(CH_2)_{6-8}CH_3$, such as —$(CH_2)_7CH[Z]$=$CH(CH_2)_7CH_3$ or —$(CH_2)_8CH[Z]$=$CH(CH_2)_7CH_3$. Preferably, Q is selected from —O—$(CH_2)_8CH[Z]$=$CH(CH_2)_7CH_3$ and —O—C(O)—$(CH_2)_7CH[Z]$=$CH(CH_2)_7CH_3$.

For the avoidance of doubt any of the optional elements of the lipids of the first aspect of the invention may be combined in further embodiments of the first aspect of the invention. For example, in one embodiment of the first aspect of the invention, the ionic compound is of the formula (Ia) where $R^1$ and $R^2$ are the same or different and are each independently a $C_{14-22}$ hydrocarbyl group; Sp and W are both bond; $R^3$ and $R^4$ each straight or branched, unsubstituted $C_{1-6}$ alkyl group; each B is selected from an unsubstituted $C_{1-3}$alkylene group; and m is 3, 4, 5, 6 or 7. Similarly, in one embodiment of the first aspect of the invention, the ionic compound is of the formula (Ib) where $R^1$ and $R^2$ are the same or different and are each independently a $C_{14-22}$ hydrocarbyl group; $R^3$ and $R^4$ each straight or branched, unsubstituted $C_{1-4}$alkyl group; each B is selected from an unsubstituted $C_{1-3}$alkylene group; and m is 3, 4, 5, 6 or 7. Again similarly, in one embodiment of the first aspect of the invention, the ionic compound is of the formula (Ic) where $R^1$ and $R^2$ are the same or different and are each independently a $C_{14-22}$ hydrocarbyl group; $R^3$ and $R^4$ each straight or branched, unsubstituted $C_{1-4}$alkyl group; and m is 3, 4, 5, 6 or 7. In a further embodiment of the first aspect of the invention, the ionic compound is of the formula (Ia) where $R^1$ and $R^2$ are the same or different and are each independently a $C_{14-20}$ hydrocarbyl group, for example, an unsaturated $C_{14-20}$ alkenyl group, having one two or three double bonds; Sp and W are both bond; $R^3$ and $R^4$ each straight or branched, unsubstituted $C_{1-4}$ alkyl group; each B is selected from an unsubstituted $C_{1-3}$alkylene group; m is 3, 4, 5 or 6; and $R^5$ is selected from a $C_{14-20}$ hydrocarbyl group, for example, an unsaturated $C_{14-20}$ alkenyl group, having one, two or three double bonds. Similarly, in a further embodiment of the first aspect of the invention, the ionic compound is of the formula (Ib) where $R^1$ and $R^2$ are the same or different and are each independently a $C_{14-20}$ hydrocarbyl group, for example, an unsaturated $C_{14-20}$ alkenyl group, having one two or three double bonds; $R^3$ and $R^4$ each straight or branched, unsubstituted $C_{1-4}$ alkyl group; each B is selected from an unsubstituted $C_{1-3}$alkylene group; m is 3, 4, 5 or 6; and R' is selected from a $C_{14-20}$ hydrocarbyl group, for example, an unsaturated $C_{14-20}$ alkenyl group, having one, two or three double bonds. Again similarly, in a further embodiment of the first aspect of the invention, the ionic compound is of the formula (Ic) where $R^1$ and $R^2$ are the same or different and are each independently a $C_{14-20}$ hydrocarbyl group, for example, an unsaturated $C_{14-20}$ alkenyl group, having one two or three double bonds; $R^3$ and $R^4$ each straight or branched, unsubstituted $C_{1-4}$ alkyl group; m is 3, 4, 5 or 6; and $R^5$ is selected from a $C_{14-20}$ hydrocarbyl group, for example, an unsaturated $C_{14-20}$ alkenyl group, having one, two or three double bonds. In a yet further embodiment of the first aspect of the invention, the ionic compound is of the formula (Ia) where $R^1$ and $R^2$ are the same or different and are each independently a straight chain, unsaturated $C_{16}$ or $C_{18}$ alkenyl group having one double bond; Sp and W are both bond; $R^3$ and $R^4$ each methyl or ethyl; each B is an ethylene group; m is 3, 4 or 5; and $R^5$ is a straight chain, unsaturated $C_{16}$ or $C_{18}$ alkenyl group having one double bond. Similarly, in a yet further embodiment of the first aspect of the invention, the ionic compound is of the formula (Ib) where $R^1$ and $R^2$ are the same or different and are each independently a straight chain, unsaturated $C_{16}$ or $C_{18}$ alkenyl group having one double bond; $R^3$ and $R^4$ each methyl or ethyl; each B is an ethylene group; m is 3, 4 or 5; and $R^5$ is a straight chain, unsaturated $C_{16}$ or $C_{18}$ alkenyl group having one double bond. Again similarly, in a yet further embodiment of the first aspect of the invention, the ionic compound is of the formula (Ic) where $R^1$ and $R^2$ are the same or different and are each independently a straight chain, unsaturated $C_{16}$ or $C_{18}$ alkenyl group having one double bond; $R^3$ and $R^4$ each methyl or ethyl; m is 3, 4 or 5; and $R^5$ is a straight chain, unsaturated $C_{16}$ or $C_{18}$ alkenyl group having one double bond.

The ionic compound of the first aspect of the invention is optionally of formula (Id):

wherein:
each of X—R$^1$ and Y—R$^2$ and Q are selected from —O—(CH$_2$)$_8$CH[Z]=CH(CH$_2$)$_7$CH$_3$ and —O—C(O)—(CH$_2$)$_7$CH[Z]=CH(CH$_2$)$_7$CH$_3$; and
m is an integer from 2 to 5.

Optionally, the ionic compound of the first aspect of the invention is of the formula (Id), wherein m is 3 or 4.

Optionally, the ionic compound of the first aspect of the invention is of the formula (Id), wherein each of X—R$^1$ and Y—R$^2$ are the same and are selected from —O—(CH$_2$)$_8$CH[Z]=CH(CH$_2$)$_7$CH$_3$ and —O—C(O)—(CH$_2$)$_7$CH[Z]=CH(CH$_2$)$_7$CH$_3$.

Optionally, the ionic compound of the first aspect of the invention is of the formula (Id), wherein each of X—R$^1$ and Y—R$^2$ are the same and are selected from —O—(CH$_2$)$_8$CH[Z]=CH(CH$_2$)$_7$CH$_3$ and —O—C(O)—(CH$_2$)$_7$CH[Z]=CH(CH$_2$)$_7$CH$_3$, Q is selected from —O—(CH$_2$)$_8$CH[Z]=CH(CH$_2$)$_7$CH$_3$ and —O—C(O)—(CH$_2$)$_7$CH[Z]=CH(CH$_2$)$_7$CH$_3$, and m is 3 or 4.

Optionally, the ionic compound of the first aspect of the invention is of the formula (Id), wherein each of X—R$^1$ and Y—R$^2$ are the same and are selected from —O—(CH$_2$)$_8$CH[Z]=CH(CH$_2$)$_7$CH$_3$ and —O—C(O)—(CH$_2$)$_7$CH[Z]=CH(CH$_2$)$_7$CH$_3$, and Q is —O—C(O)—(CH$_2$)$_7$CH[Z]=CH(CH$_2$)$_7$CH$_3$. Optionally, the lipid of the first aspect of the invention comprises a cation of the formula (Id), wherein each of X—R$^1$ and Y—R$^2$ are the same and are selected from —O—(CH$_2$)$_8$CH[Z]=CH(CH$_2$)$_7$CH$_3$ and —O—C(O)—(CH$_2$)$_7$CH[Z]=CH(CH$_2$)$_7$CH$_3$, Q is —O—C(O)—(CH$_2$)$_7$CH[Z]=CH(CH$_2$)$_7$CH$_3$, and m is 3 or 4.

The ionic compound of the first aspect of the invention typically includes an inorganic counter ion, for example, a pharmaceutically acceptable anion such as chloride or bromide.

Transfection Complexes

In a second aspect, the invention provides a transfection complex that comprises (i) a ionic compound of the first aspect of the invention. The transfection complex of the second aspect of the invention optionally further comprises a (ii) a polycationic nucleic acid-binding component and (iii) a cell surface receptor binding component. Typically, the polycationic nucleic acid-binding component (ii), and the cell surface receptor binding component (iii) together form a peptide derivative. Advantageously, the transfection complex of the second aspect of the invention further comprises (iv) a nucleic acid.

The transfection complex of the second aspect of the invention is typically a non-viral transfection complex, for example, LPD (or LID) complex.

In an eleventh aspect, the invention provides a kit that comprises:
(i) a nucleic acid,
(ii) an ionic compound of the invention as defined above,
(iii) a polycationic nucleic acid-binding component, and
(iv) a cell surface receptor binding component.

For example, the invention provides a kit that comprises:
(i) an ionic compound of the first aspect of the invention nucleic acid;
a peptide comprising (ii) a polycationic nucleic acid-binding component and (iii)
a cell surface receptor binding component; and optionally
(iv) a nucleic acid.

The kit of the eleventh aspect of the invention may, for example, be used to assemble a transfection complex of the second aspect of the invention.

In a third aspect, the invention provides a pharmaceutical composition which comprises the ionic compound of the first aspect of the invention or the transfection complex of the second aspect of the invention in admixture or conjunction with a pharmaceutically suitable carrier.

Peptides

In one embodiment, the peptide derivative of the second aspect of the invention is of the formula A-B-C wherein:
A is a polycationic nucleic acid-binding component,
B is a spacer element, and
C is a cell surface receptor binding component.

It has been found that transfection complexes of the second aspect of the invention which comprise spacer element peptide that is susceptible to cleavage within a cell are more efficient in bringing about transfection of a target cell than prior art complexes including peptides without the spacer that is susceptible to cleavage within a cell.

The polycationic nucleic acid-binding component A is any polycation that is capable of binding to DNA or RNA. A polycation may be polycationic itself or it may have any number of cationic monomers provided the ability to bind to DNA or RNA is retained. For example, from 3 to 100 cationic monomers may be present, for example, from 10 to 20, for example from 14 to 18, for example, about 16.

The term "polycationic nucleic acid-binding component" is well known in the art and refers to polymers having at least 3 repeat cationic amino acid residues or other cationic unit bearing positively charged groups, such polymers being capable of complexion with a nucleic acid under physiological conditions. An example of a nucleic acid-binding polycationic molecule is an oligopeptide comprising one or more cationic amino acids. Such an oligopeptide may, for example, be an oligo-lysine molecule, an oligo-histidine molecule, an oligo-arginine molecule, an oligo-ornithine molecule, an oligo diaminopropionic acid molecule, or an oligo-diaminobutyric acid molecule, or a combined oligomer comprising any combination of histidine, arginine, lysine, ornithine diaminopropionic acid, and diaminobutyric acid residues. Any of the above oligopeptides may have, for example, a total of from 3 to 35, for example, from 5 to 25 residues, preferably from 10 to 20 residues, for example, from 14 to 18 residues, for example 16 residues.

An oligolysine is particularly preferred, for example, having from 3 to 35, for example, from 2 to 25, for example, form 10 to 20 lysine residues, for example, from 13 to 19, for example, from 14 to 18, for example, from 15 to 17 residues, for example, 16 residues i.e. [K]$_{16}$, "K" denoting lysine.

Further examples of polycationic components include dendrimers and polyethylenimine. Polyethylenimine (PEI) is a non-toxic, cross-linked cationic polymer with gene delivery potential (*Proc. Natl. Acad. Sci.,* 1995, 92, 7297-7301). Polyethylenimine is obtainable from Fluka (800 kDa) or from Sigma (50 kDa) or alternatively pre-diluted for transfection purposes from PolyPlus-tranfection (Illkirch, France). Typically, PEI is most efficient when used in a 9 fold excess over DNA, the excess ratio being calculated as PEI nitrogen:DNA phosphate, and at pH 5 to 8. Such parameters may be optimised in a manner familiar to the person skilled in the art.

The spacer element peptide B is advantageously susceptible to cleavage within a cell. A spacer element peptide B that is susceptible to cleavage within a cell may be susceptible to cleavage within the endosome, lysosome, and/or cytoplasm of a cell. Susceptible to cleavage is understood herein to mean that the element is susceptible to cleavage over a timescale during which the components A and C remain in tact. Element B is cleaved more rapidly than the cellular peptide-degradation pathways take effect.

Preferably, the spacer element peptide is susceptible to enzymatic cleavage, reductive cleavage, or pH-dependent cleavage e.g. hydrolysis. In the case of enzymatic cleavage, in one aspect of the invention, preferred peptides are those which are susceptible to cleavage by an enzyme selected from NOX (NADH-oxidase), GILT (gamma-interferon-inducible lysosomal thiol reductase) and PDI (protein disulfide isomerase). In another aspect of the invention, preferred peptides are those which are susceptible to cleavage by an enzyme which is present in the endosome, for example an endosomal protease, such as furin or cathepsin.

Preferably the spacer element peptide B comprises a group selected from: a) a peptide chain comprising a disulfide-linkage;
  b) a peptide chain comprising an ester-linkage;
  c) an amino acid sequence susceptible to cleavage by furin; and
  d) an amino acid sequence susceptible to cleavage by a cathepsin enzyme The disulfide linkage is preferably one that is stable under normal atmospheric and physiological conditions, but that may be reductively cleaved in an endosome. Similarly, an ester linkage in a peptide chain of the invention is preferably one that is stable at neutral pH, but is cleaved in the acidic environment of an endosome (for example at pH below 6.0, preferably at pH below 5.5, or at pH below 5.0).

For example, amino acid sequences susceptible to cleavage by furin include sequences selected from
  i) $RX^1KR$; and
  ii) $RX^2RR$;
  in which $X^1$ and $X^2$, which may be the same or different, each represents any amino acid residue (Zimmer et al., *J. Biol. Chem.*, 2001, 276, 31642-31650; Nakayama, *Biochem. J.*, 1997, 327, 625-635)

Preferred amino acid residues $X^1$ include Lys (K) and Val (V), for example Lys (K). Preferred amino acid residues $X^2$ include Lys (K) and Val (V), for example Val (V).

For example, the cathepsin enzyme may be any suitable cathepsin enzyme (see Pillay et al., *Biochem. J.*, 2002, 363, 417-429). For example, it may be cathepsin B. For example, amino acid sequences susceptible to cleavage by cathepsin B (see Pechar et al., *Macromol. Chem. Phys.*, 1997, 198, 1009-1020) include sequences selected from:
  iii) $X^3X^4$ where $X^3$ is selected from Tyrosine (Tyr, Y), Phenylalanine (Phe, F), Leucine (Leu, L), Valine (Val, V) and Isoleucine (Ile, I) and $X^4$ is selected from Glycine (Gly, G), Alanine (Ala, A) and Glutamic acid (Glu, E).

Preferably, $X^3$ is selected from Tyrosine (Tyr, Y), Phenylalanine (Phe, F) and Leucine (Leu, L).

For example, the sequence $X^3X^4$ may be present as $GFX^3X^4$, for example as GFLG (as used in Pechar et al., *Bioconjugate Chem.*, 2000, 11, 131-139)

The spacer element peptide B may additionally comprise a linker, which is preferably either a peptide, that is to say, it comprises amino acid residues, or a polyethyleneglycol group, or a mixture of the two. The amino acids may be naturally occurring or non-naturally occurring. They may have L- or D-configuration. The linker may have two or more amino acids. It may, for example, comprise three or more amino acids, for example, four or more, for example, five or more, for example, up to ten amino acids or more. The amino acids may be the same or different, but the use of multiple lysine residues (or other cationic amino acids suitable for use in the polycationic nucleic acid-binding component of a vector complex) should generally be avoided in the spacer as oligo-lysine sequences have activity as a polycationic nucleic acid-binding component.

The linker may be, for example, the dipeptide glycine-glycine (GG) or glycine-alanine (GA).

The linker may be, or may include a polyethyleneglycol moiety. The polyethyleneglycol moiety may comprise from 1 to 30 ethylene glycol units, preferably from 1 to 15 units, more preferably from 1 to 8 units, for example from 2 to 6 units, for example 4 units.

Preferably, the linker is at the end of the spacer element peptide B which is bonded to the polycationic nucleic acid-binding component A.

Preferably the cell surface receptor binding component C comprises a peptide. Where cell surface receptor binding component C comprises a peptide, the peptide may be up to 20 amino acids in length, or may be longer. The peptide generally has at least 5 amino acids but may have fewer. Generally, the peptide has any number of amino acids from 6 to 20 inclusive. Generally, it is preferred for the peptide to have 15 amino acids or fewer, more preferably 12 amino acids or fewer, most preferably 10 amino acids or fewer. Generally, it is preferred for the peptide to have 5 or more amino acids, for example, 6 or more amino acids. Most preferably, the peptide has 7 amino acids.

Preferably the cell surface receptor binding component C comprises a peptide comprising a cyclic region. Cyclic peptides may be formed by the provision of at least two cysteine residues in the peptide, thus enabling the formation of a disulphide bond. Accordingly, preferred cell surface receptor binding components C consist of or comprise a peptide having two or more cysteine residues that are capable of forming one or more disulphide bond(s). Preferably the cysteine residues flank the primary receptor binding portion.

In one embodiment of the invention, the cell surface receptor binding component C comprises an integrin-binding peptide. An integrin-binding peptide is any peptide that is capable of binding specifically to integrins found on the surface of cells. The integrin-binding peptide may be a naturally occurring integrin-binding ligand, for example, an extracellular matrix protein, a viral capsid protein, the bacterial protein invasin, a snake venom disintegrin protein, or an integrin-binding fragment of any such protein. Such integrin-binding proteins and fragments thereof may be obtained from natural sources or by recombinant techniques. It is preferable to use integrin-binding peptides, in particular because of their ease of synthesis, purification and storage, their potential for chemical modification, and their potentially low immunogenicity in vivo. Preferred integrin-binding peptides are those such as described in WO 96/15811, and especially WO 98/54347. For example, an integrin-binding peptide may be specific for α4β1 integrins.

In this embodiment, the cell surface receptor binding component C preferably comprises a peptide selected from:
  a) RGD;
  b) RRETAWA;
  c) LDV In a further embodiment of the invention, the cell surface receptor binding component C comprises a peptide which is capable of binding to human airway epithelial (HAE) cells. Preferred HAE cell-binding peptides are those such as described in WO 02/072616. In this embodiment, the cell surface receptor binding component C preferably comprises a peptide selected from
  a) $X^5SM$;
  b) $LX^6HK$;
  c) $PSGX^7ARA$;

d) SX$^8$RSMNF; and
e) LX$^9$HKSMP;

in which X$^5$ is a basic amino acid residue, X$^6$ is Q or P, X$^7$ is A or T, X$^8$ is an acidic amino acid residue and X$^9$ is P or Q.

Preferably, the cell surface receptor binding component C comprises a peptide selected from
a) X$^5$SM;
b) LX$^6$HK; and
c) PSGAARA, in which X$^5$ is a basic amino acid residue and X$^6$ is Q or P.

Preferably X$^5$ is K or R. Preferably X$^6$ is P. Preferably X$^7$ is A. Preferably X$^8$ is E or Q. More preferably X$^8$ is E. Preferably X$^9$ is P. Accordingly, preferred peptides are those comprising a sequence selected from LQHKSMP, LPHKSMP, VKSMVTH, SERSMNF, VGLPHKF, YGLPHKF, PSGAARA, SQRSMNF and PSGTARA.

In another embodiment of the invention, the cell surface receptor binding component C comprises a peptide which is capable of binding to human dendritic cells. Preferred human dendritic cell-binding peptides are those such as described in WO 2004/108938. For example, such a peptide may be selected from a peptide comprising an amino acid sequence selected from:
a) PX$^{10}$X$^{11}$X$^{12}$T;
b) PSX$^{13}$S;
c) QX$^{14}$X$^{15}$X$^{16}$Q;
d) SX$^{17}$S, in which X$^{10}$, X$^{11}$ and X$^{12}$, which may be the same or different, each represents an amino acid residue;

X$^{13}$ represents an amino acid residue;

X$^{14}$ and X$^{16}$, which may be the same or different, each represents an amino acid residue, and X$^{15}$ represents an amino acid residue having an amide side chain, for example, N or Q.

X$^1$ represents an amino acid residue having an aliphatic side chain, for example, L or I.

In a preferred embodiment, the cell surface receptor binding component C comprises a peptide selected from:

a) CRGDCLG;
b) CRGDCLG;
c) ACDCRGDCFCG;
d) CRGDMFGCA;
e) CRRETAWACG;
f) CRGEMFGCA;
g) CSERSMNFCG;
h) CYGLPHKFCG; and
i) CLPHKSMPCG.

The invention provides the use of a transfection complex of the second aspect of the invention in the formation of a lipopolyplex (LPD) transfection vector. The transfection vector may be used to target an entity to a cell, the entity being a nucleic acid or another molecule, for example, a therapeutically or pharmaceutically active molecule, or a molecule comprising a detectable label.

Medical Uses

It has further been found that an ionic compound of the invention improves the targeting of a vector complex to tumour cells, particularly when used in conjunction with a cleavable peptide. The ionic compound of the first invention thus finds use in the treatment of cancer, therapeutic or prophylactic immunisation, or anti-sense or RNAi therapy. The invention thus provides a method of treating cancer, therapeutic or prophylactic immunisation, or anti-sense or RNAi therapy comprising administering an ionic compound of the first aspect of the invention in a suitable complex to the patient in an effective amount. The transfection complexes of the second aspect of the invention thus find use in the treatment of cancers, for therapeutic or prophylactic immunisation, or for anti-sense or RNAi therapy. The invention thus provides a method of treating cancer, therapeutic or prophylactic immunisation, or anti-sense or RNAi therapy comprising administering a transfection complex of the second aspect of the invention to the patient in an effective amount. The ionic compound of the first aspect of the invention or the transfection complex of the second aspect of the invention may be administered in a pharmaceutical composition of the third aspect of the invention, which comprises the ionic compound or transfection complex in admixture or conjunction with a pharmaceutically suitable carrier.

In a fourth aspect, the invention provides an ionic compound of the first aspect of the invention or a transfection complex of the second aspect of the invention for use in therapy. The invention further provides an ionic compound of the first aspect of the invention or a transfection complex of the second aspect invention for use as a medicament or a vaccine. For example, the fourth aspect of the invention provides an ionic compound of the first aspect of the invention or a transfection complex of the second aspect of the invention for use in the treatment or prophylaxis of condition caused by a defect and/or a deficiency in a gene, for use in the treatment of cancer, for therapeutic or prophylactic immunisation, or for anti-sense or RNAi therapy.

The nucleic acid component (D) may be any suitable nucleic acid. It may be DNA or RNA or a chemically modified nucleic acid mimetic, for example a PNA molecule. It may, for example, code for a protein that has a utility in the target cell. It may be an anti-sense nucleic acid or an RNAi nucleic acid. RNAi is achieved by exposing the cellular messenger RNA (mRNA) molecules produced by the target gene to double-stranded RNA (dsRNA) molecules that contain sequences complementary to a short portion of the mRNA molecule. Inside the cell, the double-stranded RNA molecules are cleaved to produce short (21-23 nucleotides long) single and double-stranded fragments which can bind to the target mRNA molecules. Such binding leads to the cleavage of the target mRNA by nucleases, thus resulting in a reduction in the expression levels of the target gene. Thus the nucleic acid component may itself be an RNAi molecule (an "siRNA"); alternatively, the nucleic acid administered may be a DNA molecule that comprises a sequence that, when transcribed, produces an RNAi molecule, i.e. an RNA that is capable of suppressing the expression of a target gene via RNA interference.

The invention also provides processes for the production of a transfection complex of the invention.

In a fifth aspect, the invention provides a method for the treatment or prophylaxis of a condition caused in a human or in a non-human animal by a defect and/or a deficiency in a gene which comprises administering the ionic compound of the first aspect of the invention or the transfection complex of the second aspect invention the human or to the non-human animal.

The term "a defect and/or a deficiency in a gene" as used herein denotes not only a defect or deficiency in the coding region of a gene, but a defect or deficiency in a control element for the gene, for example, a control element in trans or in cis, or a defect or deficiency in any other element that is involved in the transcription or translation of the gene, whether directly or indirectly.

In a sixth aspect, the invention provides a method for therapeutic or prophylactic immunisation of a human or of a non-human animal, which comprises administering the ionic compound of the first aspect of the invention together with, or the transfection complex of the second aspect of the invention comprising, an anti-sense nucleic acid (for example anti-sense RNA) or a nucleic acid suitable for RNAi therapy to the human or to the non-human animal. The invention also provides a method of anti-sense therapy, which comprises administering the ionic compound of the first aspect of the invention together with a nucleic acid, or a transfection complex of the second aspect invention comprising nucleic acid, to a human or to a non-human animal in which the nucleic acid is a nucleic acid (for example RNA) suitable for use in anti-sense therapy or a nucleic acid suitable for RNAi therapy.

EXAMPLES

Unless otherwise noted, solvents and reagents for synthesis were reagent grade from commercial suppliers and used without further purification. Dry $CH_2Cl_2$ was obtained using anhydrous alumina columns using the procedure described in Pangborn, A. B.; Giardello, M. A.; Grubbs, R. H.; Rosen, R. K.; Timmers, F. J. *Organometallics* 1996, 15, 1518-1520. All moisture-sensitive reactions were performed under a nitrogen or argon atmosphere using oven-dried glassware. Reactions were monitored by TLC on Kieselgel 60 $F_{254}$ plates with detection by UV, potassium permanganate, and phosphomolybdic acid stains. Flash column chromatography was carried out using silica gel (particle size 40-63 μm). $^1H$ NMR and $^{13}C$ NMR spectra were recorded on a Bruker AMX300 MHz, Avance-500 MHz and Avance-600 MHz machines. Coupling constants are measure in Hertz (Hz) and unless otherwise specified, spectra were acquired at 298 K. Mass spectra were recorded on Thermo Finnegan MAT 900XP, Micromass Quattro LC electrospray and VG70-SE mass spectrometers. Infrared spectra were recorded on a Shimadzu FTIR-8700 spectrometer.

DODEG4 (13)

{2,3-di[(Z))-octadecy-9-enyloxy]-propyl}-N-{2-[2-(2-{2-hydroxy-ethoxy}-ethoxy)-ethoxy]-ethyl}-N,N-dimethylammonium chloride (DODEG4) (13) (CH300) was synthesized as previously reported by Dori, Y.; Bianco-Peled, H.; Satija, S.; Fields, G. B.; McCarthy, J. B.; Tirrell, M. *J. Biomed. Mater. Res.* 2000, 50, 75-81, from (2,3-bis-octadec-9-enyloxypropyl)-dimethylamine and 4-EG bromide (HO—$(CH_2CH_2$—$O)_3$—$CH_2CH_2$—Br).

DODEG4 13

DODEG4 (13) (CH300) can also be synthesis as described in U.S. Pat. No. 7,598,421, Example 4.

Analogues to DODEG4

Salts similar to DODEG4 (13) (CH300) with $R^1$ and $R^2$ hydrocarbyl groups of differing chain lengths and with different values for m, i.e. differing polyethylene glycol chain lengths, may be prepared as described in U.S. Pat. No. 7,598,421 (see Examples 3, 5, 6 and 7 in particular). For example, DODEG3 can be synthesized by the protocol set of Example 3 of U.S. Pat. No. 7,598,421.

DODEG3

DOesDEG4 (15)

The diester analogue DOesDEG4 (15) was prepared similarly to DODEG4 (13) via the quaternisation of (2,3-bis-heptadec-9-enylcarboxypropyl)-dimethylamine with 4-EG bromide.

Tertiary Amine (16)

2,3-di-((9Z)-octadecenyloxy)propyl-N,N-dimethylamine (16) is prepared as described in Hurley, C. A.; Wong, J. B.; Hailes, H. C.; Tabor, A. B. *J. Org. Chem.* 2004, 69, 980-983 from octadec-9-enyl mesylate and 3-dimethylamino-1,2-propanediol.

4-EG Bromide (17)

11-Bromo-3,6,9-trioxoundecan-1-ol (17) was prepared as described in Hurley, C. A.; Wong, J. B.; Ho, J.; Writer, M.; Irvine, S. A.; Lawrence, M. J.; Hart, S. L.; Tabor, A. B.; Hailes, H. C. *Org. Biomol. Chem.* 2008, 6, 2554-2559.

4-EG Oleoyl Ester (20)

4-EG oleoyl ester (20) was prepared by the reaction of 4-EG bromide (17) with oleic acid, in the presence of DMAP and DIC in $CH_2Cl_2$.

A solution of oleic acid (2.00 mL, 6.30 mmol), the 4-EG bromide 17 (1.50 g, 5.83 mmol), and DMAP (70 mg, 0.58 mmol) in anhydrous dichloromethane (50 mL) were stirred for at rt for 5 min. After cooling to 0° C., N,N'-diisopropylcarbodiimide (DIC) (1.20 mL, 7.75 mmol) was added dropwise and the mixture stirred at rt for 18 h. The dichloromethane was removed in vacuo, ethyl acetate (60 mL) was added, and the mixture washed with sodium hydrogencarbonate (2×60 mL), brine (60 mL), dried ($Na_2SO_4$) and concentrated in vacuo. Purification by silica flash chromatography (EtOAc/hexane, 1:4) yielded 20 as a yellow oil (1.65 g, 54%). $R_F$ 0.19 (EtOAc/hexane, 1:4); $v_{max}$(neat)/$cm^{-1}$ 2923, 1736, 1457; $^1$H NMR (300 MHz; $CDCl_3$) δ 0.84 (t, J=6.7 Hz, 3H), 1.18-1.30 (m, 20H), 1.58 (m, 2H), 1.93-2.00 (m, 4H), 2.29 (t, J=7.6 Hz, 2H), 3.43 (t, J=6.3 Hz, 2H), 3.59-3.67 (m, 10H), 3.77 (t, J=6.3 Hz, 2H), 4.19 (t, J=4.8 Hz, 2H), 5.27-5.36 (m, 2H); $^{13}$C NMR (75 MHz; $CDCl_3$) δ 14.1, 22.6, 24.9, 27.2, 29.1-29.8 (signals superimposed), 30.4, 31.9, 34.0, 63.3, 69.2, 70.4-70.6 (signals superimposed), 71.2, 129.7, 130.0, 173.6; m/z [HRMS ES+] found [MNa]$^+$ 543.2671. $C_{26}H_{49}O_5^{79}BrNa$ requires 543.2661.

TC-DODEG4 (14)

TriChain ionic compound (9Z)—N-(2,3-bis((9Z)-octadecenyloxy)propyl)-N,N-dimethyl-13-oxo-3,6,9,12-tetraoxatriacont-21-en-1-aminium bromide (TC-DODEG4) (14) was synthesised by the quaternisation of (2,3-bis-octadec-9-enyloxypropyl)-dimethylamine (16) with the 4-EG oleoyl ester (20).

A solution of the amine (16) (0.260 g, 0.420 mmol) and the 4-EG oleoyl ester (20) (0.240 g, 0.460 mmol) in acetone (2 mL) were stirred in a sealed tube at 90° C. for 48 h. The acetone was removed in vacuo. Purification by flash silica chromatography ($CH_2Cl_2$/MeOH, 19:1) yielded TC-DO-DEG4 (14) as a pale yellow oil (171 mg, 36%). $R_F$ 0.40 ($CH_2Cl_2$/MeOH, 9:1); $v_{max}$ (neat)/$cm^{-1}$ 2950, 2859, 1740, 1464; H NMR (600 MHz; $CDCl_3$) δ 0.83 (t, J=7.0 Hz, 9H), 1.13-1.22 (m, 64H), 1.51 (m, 4H), 1.57 (m, 2H), 1.92-1.97 (m, 12H), 2.29 (t, J=7.7 Hz, 2H), 3.38-3.51 (m, 14H), 3.51 (m, 6H), 3.58 (m, 4H), 3.92-4.05 (m, 4H), 4.08 (m, 1H), 4.18 (m, 2H), 5.27 (m, 6H); $^{13}$C NMR (150 MHz; $CDCl_3$) δ 14.2, 22.8, 25.0, 26.1, 26.3, 27.26, 27.30, 29.0, 29.1-29.9 (signals superimposed), 30.1, 32.1, 32.7, 34.2, 53.3, 53.4, 63.3, 65.0, 65.2, 66.8, 68.6, 69.29, 69.32, 70.3, 70.4, 70.5, 70.6, 72.1, 73.5, 127.9-130.5 (signals superimposed), 173.9; m/z [HRMS ES+] found [M-Br]$^+$ 1060.9904. $C_{67}H_{130}NO_7$ requires 1060.9847; m/z (+ES) 1061 ([M-Br]$^+$, 100%), 980 (60), 931 (70), 843 (65), 306 (63).

Tertiary Amine (18)

(9Z)-3-(dimethylamino)propane-1,2-diyl dioleate (18) was prepared as described in Narang, A. S.; Thoma, L.; Miller, D. D.; Mahato, R. I. *Bioconjugate Chem.* 2005, 16, 156-168.

TC-DOesDEG4 (19)

TriChain ionic compound (9Z)—N,N-dimethyl-N-(3-(oleoyloxy)-2-((9Z)-2-oxooctadecenyloxy) propyl)-13-oxo- 3,6,9,12-tetraoxatriacont-21-en-1-aminium bromide (TC-DOesDEG4) (19) was synthesised by the quaternisation of (2,3-bis-heptadec-9-enylcarboxypropyl)-dimethylamine (18) with the 4-EG oleoyl ester (20).

A solution of the amine 18 (0.610 g, 0.941 mmol) and the 4-EG oleoyl ester 20 (0.640 g, 1.22 mmol) in acetone (2 mL) were stirred in a sealed tube at 80° C. for 48 h. The acetone was removed in vacuo. Purification by flash silica chromatography ($CH_2Cl_2$/MeOH, 19:1) yielded 19 as a pale yellow oil (118 mg, 11%). $R_F$ 0.24 ($CH_2Cl_2$/MeOH, 19:1); $v_{max}$ (neat)/$cm^{-1}$ 2924, 2854, 1740, 1465; $^1$H NMR (500 MHz; $CDCl_3$) δ 0.86 (t, J=6.8 Hz, 9H), 1.25-1.32 (m, 60H), 1.58 (m, 6H), 1.99 (m, 12H), 2.30 (t, J=7.5 Hz, 4H), 2.34 (m, 2H), 3.44 (s, 3H), 3.51 (s, 3H), 3.64-3.68 (m, 11H), 3.82 (dd, J=13.5 and 10.0 Hz, 1H), 3.94 (m, 2H), 4.05 (m, 2H), 4.13 (m, 1H), 4.20 (t, J=5.0 Hz, 2H), 4.35 (d, J=13.5 Hz, 1H), 4.48 (dd, 0.1=12.3 and 3.3 Hz, 1H), 5.28-5.35 (m, 6H), 5.64 (m, 1H); $^{13}$C NMR (125 MHz; $CDCl_3$) δ 14.2, 22.7, 24.7, 24.8, 25.0, 25.7, 27.2, 27.3, 29.1-29.8, 31.6, 32.0, 34.0, 34.3, 52.8, 52.9, 63.2, 63.3, 64.0, 64.9, 65.6, 65.8, 69.3, 70.1, 70.45, 70.48, 70.6, 129.7-130.1 (signals superimposed), 172.9, 173.2, 173.8; m/z [HRMS ES+] found $[M-Br]^+$ 1088.9382. $C_{67}H_{126}NO_9$ requires 1088.9433; m/z (+ES) 1089 ($[M-Br]^+$, 100%).

Analogues to TC-DOesDEG4

Tri-chain lipids TC-DODEG3 and TC-DOesDEG3, in which m=2 may similarly be synthesised by the quaternisation of (2,3-bis-octadec-9-enyloxypropyl)-dimethylamine (16) and (2,3-bis-heptadec-9-enylcarboxypropyl)-dimethylamine (18) respectively with the 3-EG oleoyl ester.

Lipid ME42 (Comparative)

(2,3-Bis-octadec-9-enyloxypropyl)(8-hydroxy-3,6-dioxooctyloxycarbonylbutyl)-dimethylammonium bromide (ME42) was prepared as described in WO 2007/138324 (see pages 41 and 42).

Lipid DHDTMA (106a) (Comparative)

DHDTMA is a cationic lipid based on a glycerol backbone with two unsaturated C16 alkyl chains linked by diether linkages described in Writer M, Hurley C A, Sarkar S, Copeman D M, Wong J B, et al. *Analysis and optimization of the cationic lipid component of a lipid/peptide vector formulation for enhanced transfection in vitro and in vivo*. J Liposome Res. 2006; 16:373-389.

Peptide Synthesis

The peptides described (Table IA) were synthesized using standard instruments and techniques.

TABLE IA

| Peptide sequence | |
|---|---|
| Peptide | Sequence |
| K16 | KKKKKKKKKKKKKKKK |
| ME27 | (K)$_{16}$RVRRGACRGDCLG |
| K16CY | (K)$_{16}$RVRRGACYGLPHKFCG |
| K16Y | (K)$_{16}$GACYGLPHKFCG |
| K16P | (K)$_{16}$GACLPHKSMPCG |

TABLE IB

| Peptide mass | |
|---|---|
| Peptide | Mass (g · mol$^{-1}$) |
| K16 | 2068 |
| ME27 | 3467.5 |
| K16CY | 3871 |

ME42

Lipid FMM32 (Comparative)

TABLE IB-continued

| Peptide | Mass (g · mol⁻¹) |
|---|---|
| K16Y | 3326.8 |
| K16P | 3148.1 |

ME27 was synthesized on a SYRO automated peptide synthesizer.

Linear peptide sequences: The peptide was synthesized on a 20 µmol scale using 2 ml syringes with Teflon frits and 500 µl coupling volume. Fmoc-Gly preloaded NovaSyn TGT resin or Fmoc-Gly-2-Cl-Trt-resin were used for these sequences. Fmoc-Peg4-COOH was synthesized following a procedure reported previously (see synthesis of Fmoc-Haa4-COOH at page 82 of WO 2005/117985—Fmoc-Haa4-COOH was the name given to Fmoc-Peg4-COOH in that specification). The TGT resin was initially swelled for 10 min, however the 2-Cl-Trt resin needed a prolonged initial swelling time (some hours) in DMF. Routine coupling was performed with HBTU (in DMF) and DIPEA (in NMP) using a fourfold excess of reagents. Fmoc was cleaved with a 40% solution of piperidine in DMF for 3 min and a 20% solution for 10 min. Synthesis cycles consisted of 40 min coupling time, 3 min for Fmoc deprotection with 40% piperidine, another 10 min for Fmoc deprotection with 20% piperidine and washing steps. After synthesis and the last wash cycle with DMF, peptides were washed with DCM, methanol and diethyl ether (3 times each) using the "manual"/"empty" function of the Syro. Suction was applied for some more time to help evaporate the ether.

On-resin disulfide bond formation: To form disulphide bridges on resin, the resin was placed in a syringe with PE frit and swelled in DMF. After removal of excess DMF a freshly prepared solution of iodine in a minimum amount of DMF (e.g. 500 µl for a 2 ml syringe, 10 eq iodine to resin loading) was added and the syringe was vortexed during 4 h for 20 s every 4 min. The reagent solution was removed and the resin was washed 10 to 20 times with DMF, and 3 times each with DCM, methanol and ether.

Cleavage and deprotection: The syringes were transferred to the fume hood for cleavage. Cleavage was performed with a cocktail of 95% TFA, 2.5% TIS and 2.5% $H_2O$. A minimum amount of freshly prepared cocktail was added to cover the resin (e.g. <500 µl in the 2 ml syringes). After 4 h the cleavage solutions were passed into polypropylene (PP) tubes using a plunger and the resins were washed with another small amount of cleavage cocktail (e.g. 200 µl in the 2 ml syringes). Then the peptides were precipitated with ether (e.g. to the combined fractions of the 2 ml syringes some 4 ml of diethyl ether were added). The PP tubes were kept in the freezer for at least 15 min, then centrifuged at 3000 rpm for 3 min and solution was decanted from the peptide pellet. Centrifugation and decantation were repeated twice with about 2 ml of ether. Finally the peptides were dissolved in water or tBuOH/water (4:1) and freeze-dried. Some peptide sequences showed very poor solubility and sometimes several lyophilisation/dissolution processes with different solvent mixtures (water, tBuOH or acetonitrile) were necessary to obtain a fluffy peptide.

The peptide was analyzed by reverse phase HPLC and purified by reverse phase HPLC to >90% pure. Mass spectra were recorded using the Micromass Quattro ES-MS (Software: Masslynx) and the masses are recorded in the table IB.

K16CY, K16Y and K16P were purchased from AMS Bio Ltd., Birmingham, UK, and synthesised using semi-automated peptide synthesis chemistry. The peptide was analysed by reverse phase HPLC and purified where necessary by reverse phase HPLC to 85% pure. Relative molecular masses are given in the table IB.

K16 was purchased as described previously (Hart et al., Lipid-mediated enhancement of transfection by a nonviral integrin-targeting vector. *Hum Gene Ther.,* 1998, 9, 575-585). Relative molecular masses are given in the table IB.

All these freeze-dried peptides were diluted at 10 mg/ml in water and stored at −20° C. during several months. Once thawing, aliquots of peptides are kept at 4° C. during several weeks.

Plasmid DNA

The plasmid pCI-Luc (5.7 kb) consists of pCI (Promega, Southampton, UK) containing the luciferase gene driven by the cytomegalovirus (CMV) immediate/early promoter-enhancer. The plasmids were grown in *Escherichia coli* DH5α and purified, after bacterial alkaline lysis, on resin columns (Qiagen Ltd., Crawley, UK). Isopropanol-precipitated DNA pellets were washed with 70% ethanol, then dissolved in water at 1 mg/ml.

In Vitro Transfection

Cells tested included 1HAEo-human airway epithelial cells, NIH3T3 murine fibroblasts, and Neuro2A murine neuroblastoma cells. Cells were seeded into 96-well plates at approximately $2 \times 10^4$ cells per well, then incubated overnight at 37° C. in complete growth medium. The following day, lipopolyplex (LPD) formulations were prepared essentially as described previously (Hart et al., 1998), by mixing the components in the following order: 50 µl of lipid (L) at 80 µg/ml in OptiMEM, 70 µl of peptide (P) at 110 µg/ml in OptiMEM and 50 µl of plasmid pCI-Luc (D) at 40 µg/ml in OptiMEM corresponding to a weight ratio of 2:4:1, respectively. All the complexes were mixed by pipetting briefly, kept for 1 h at room temperature and then diluted in OptiMEM to a final volume of 1.57 ml. Two hundred microlitres of complexes corresponding at 0.25 g of plasmid DNA were added to each culture well after removal of the complete growth medium. All the transfections were carried out in 6 wells each. A centrifugation (1500 rpm, during 5 minutes) could be performed to promote the complex sedimentation and cell contact. The cells were incubated with the complexes for 4 h at 37° C. before replacing with fresh media for 24 h, after which reporter gene expression was analyzed by luciferase assay (Promega, Madison, Wis., USA).

Unless otherwise specified, cationic liposomes comprising mixtures of two ionic compounds, e.g. FMM30 and DOPE, comprise the ionic compounds in a 1:1 ratio.

NIH3T3 and 1HAEo-cells were transfected with LPD formulations containing peptide ME27 and plasmid pCI-Luc and one of the lipid formulations:

CH300/DOPE in a molar ratio of 1:1,
FMM30/DOPE in a molar ratio of 1:1,
CH300/FMM30/DOPE in a molar ratio of 4:1:5,
CH300/FMM30/DOPE in a molar ratio of 1:1:2,
FMM32/DOPE in a molar ratio of 1:1.

As a positive control cells were transfected with the commercial transfection reagent Lipofectamine 2000 (L2K purchased from Life Technologies Inc.). Total lipid:peptide:DNA ratios were 1:4:1, 2:4:1 or 4:4:1. LPD formulations were all prepared by mixing in the order L:P:D as described above. The results are displayed in FIG. 1 and FIG. 2.

LPD formulations containing different combinations of lipids were prepared with four different peptides, ME27, K16CY, K16Y and K16P, and used to transfect NIH3T3 cells with pCI-Luc as described above. The lipids used were:
CH300/DOPE in a molar ratio of 1:1,
FMM30/DOPE in a molar ratio of 1:1,
CH300/FMM30/DOPE in a molar ratio of 4:1:5,
CH300/FMM30/DOPE in a molar ratio of 1:1:2,
FMM32/DOPE in a molar ratio of 1:1,
106a (DHDTMA)/DOPE in a molar ratio of 1:1, and
DOTMA/DOPE in a molar ratio of 1:1.

The commercial reagents DOTAP, Lipofectin and Lipofectamine 2000 (L2K) were also compared in LPD combination with peptides and DNA. All L:P:D weight ratios were 2:4:1 and wells each received 0.25 μg of pCI-Luc. The results are displayed in FIG. 3.

LPD formulations containing different lipids ME42/DOPE (ME42), CH300/DOPE(CH300) or FMM30/DOPE were prepared with either the targeting peptides ME27 or K16Y and used to transfect Neuro-2A murine neuroblastoma cells. The results are displayed in FIG. 4. (N.b references to peptide "Y" in FIG. 4 should more correctly refer to "K16Y" as the peptide tested included a polylysine moiety together with the GACYGLPHKFCG "Y" core motif).

Luciferase and Protein Assays

Cells were washed once with PBS before the addition of 20 μl of 1× Reporter Lysis Buffer (Promega, Madison, Wis., USA) to the cells for 20 min at 4° C. before freezing at −80° C. for at least 30 min, followed by thawing at room temperature. Then the luciferase activity was measured during 10 seconds using the Luciferase Assay System (Promega, Madison, Wis., USA) and an Optima Fluostar plate reader (BMG Labtech). The amount of protein present in each transfection lysate was determined with the Bio-Rad (Hercules, Calif., USA) protein assay reagent by the manufacturer's instructions, adding 20 μl from the luciferase test to 180 μl of the reagent diluted 1 in 5 and incubating at room temperature for 10 min before comparing the OD590 to a range of BSA standards. In vitro luciferase activity was expressed as Relative Light Units (RLU) per milligram of protein (RLU/mg).

Particle Imaging

Figure 5:
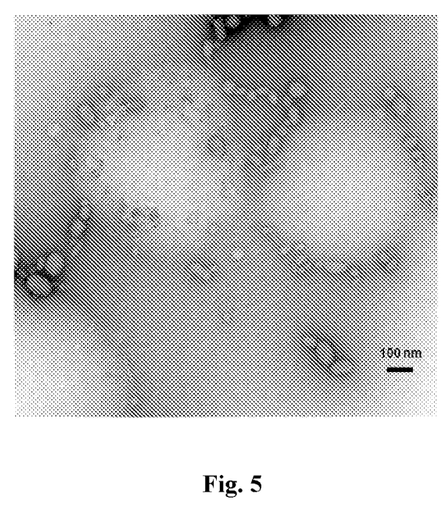
FIG. 5 shows transmission electron microscope (EM) images of LPD particles comprising FMM30 with peptide ME27 at a weight ratio of 0.75:4:1 (L:P:D).
Figure 6:
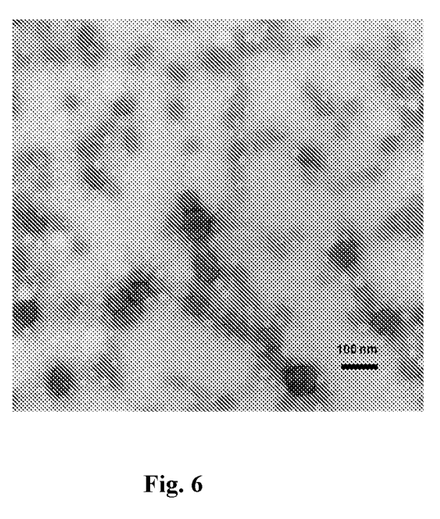
FIG. 6 shows transmission electron microscope (EM) images of LPD particles comprising FMM30/DOPE with peptide ME27 at a weight ratio of 0.75:4:1 (L:P:D).

Transmission Electon Microscope images of LPD particles comprising FMM30 with peptide ME27 at a weight ratio of 0.75:4:1 (L:P:D) is shown in FIG. 5 (FMM30-PD-0.75) and lipids FMM30/DOPE at the same weight ratio is shown in FIG. 6 (FMM30/DOPE-PD 0.75).

Figure 7:
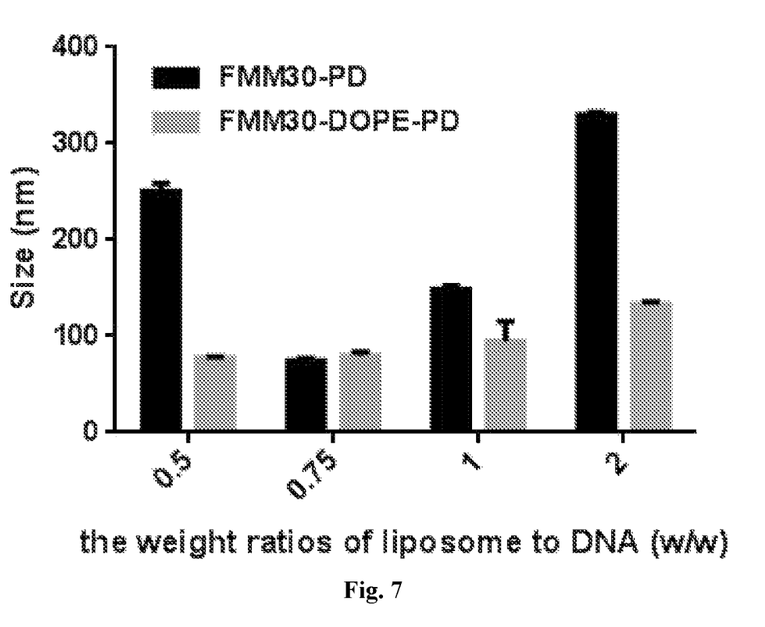
FIG. 7 shows the size of LPD nanoparticles containing peptide ME27 with lipids FMM30 or FMM30/DOPE lined at different weight ratios of liposome to DNA (w/w).

The size of LPD nanoparticles containing peptides ME27 with lipids FMM30 or FMM30/DPE were determined at different weight ratios of liposome to DNA (w/w) by dynamic light scattering using a NanoZS Zetasizer (Malvern). The results are shown in FIG. 7.

Results and Discussion

In Vitro Transfection Efficiency of Lipids in NIH3T3 and 1HAEo-Cells

Figure 1:
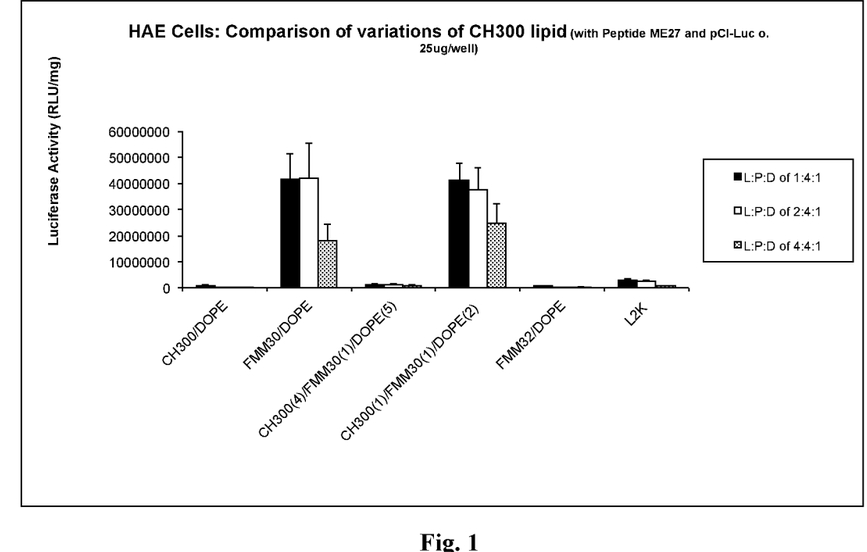
FIG. 1 shows transfections of NIH3T3 cells with LPD formulations containing the peptide ME27 and plasmid pCI-Luc in combination with a PEG-ester cleavable lipid (ME42), a PEG-ester non-cleavable lipid (CH300), a Tri-chain PEG-ester lipid of the invention (FMM30), or an ME42-related lipid with oleoyl linked by an ester bond (FMM32), some of which were in combination with the neutral, fusogenic lipid DOPE.
Figure 2:
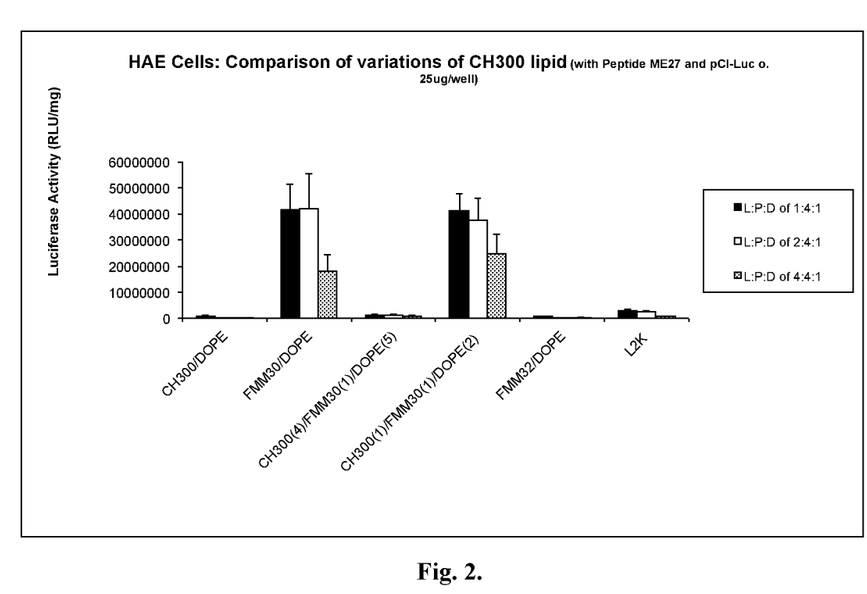
FIG. 2 shows the result of the same experiment as described in FIG. 1 but performed with a second cell line, 1HAEo-.

FIG. 1 and FIG. 2 show that transfection levels using the LPD formulations containing the tri-chain ionic compound FMM30 were far higher than the bi-chain lipid CH300 in both NIH3T3 and 1HAEo-cell lines. LPD formulations containing mixtures of lipids (CH300/FMM30/DOPE) at a high ratio of FMM30 also worked well compared to those that contained a small proportion of FMM30. The formulations containing FMM32/DOPE gave similarly low levels of transfection to CH300/DOPE formulations.

Figure 3:
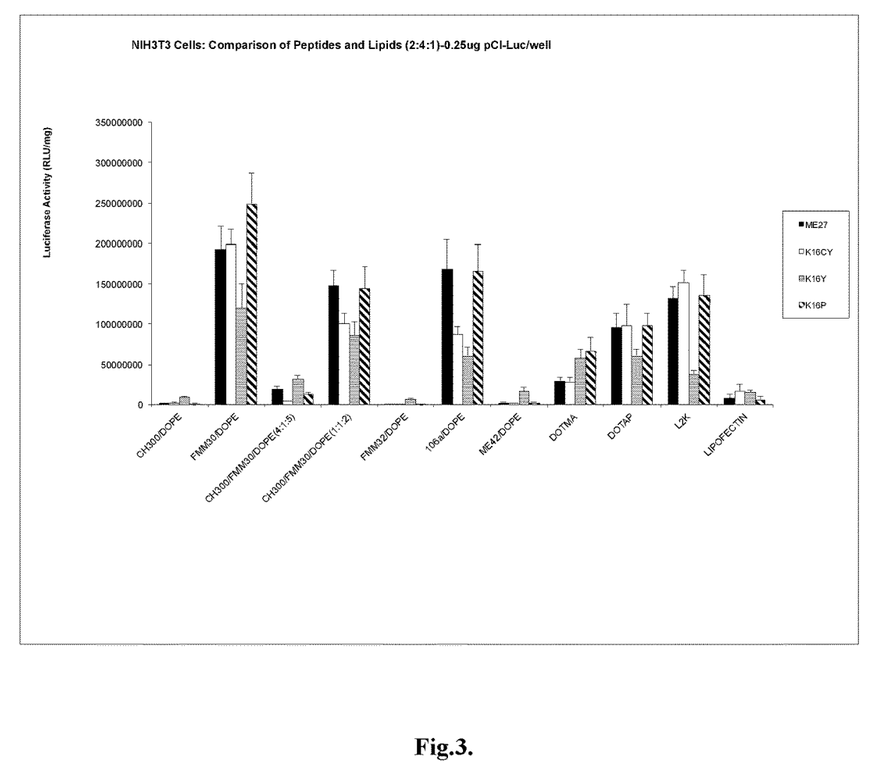
FIG. 3 shows transfection with LPD formulations containing a PEG-ester cleavable lipid (ME42), a PEG-ester non-cleavable lipid (CH300) or a Tri-chain PEG-ester lipid of the invention (FMM30), an ME42-related lipid with oleoyl linked by an ester bond (FMM32), a diester, unsaturated lipid with C16 alkyl tail (106a), some of which were in combination with the neutral, fusogenic lipid DOPE. Lipids were combined with peptides ME27, K16CY, K16Y and K16P and used to transfect NIH3T3 cells with pCI-Luc.

FIG. 3 shows that formulations for each peptide in a FMM30/DOPE-containing LPD formulation produced the highest levels of transfection and transfection levels for FMM30/DOPE-containing LPD formulations were higher than all three commercial reagents as well as the C16 lipid 106a, previously shown to be optimal for transfection.

In Vitro Transfection Efficiency of Lipids in Neuro 2A Cell Lines

Figure 4:
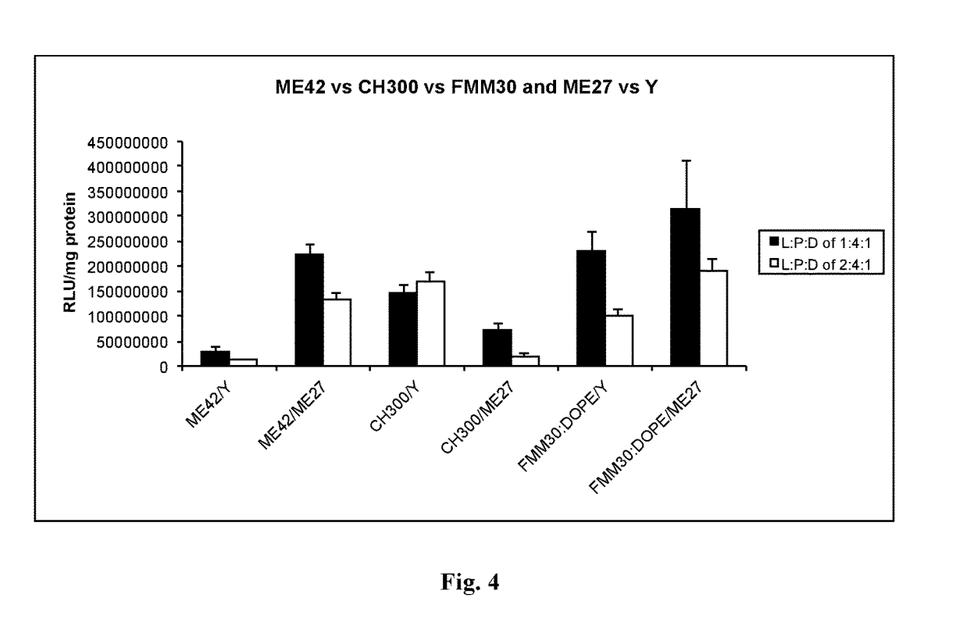
FIG. 4 shows transfection with LPD complexes containing a PEG-ester cleavable lipid (ME42), a PEG-ester non-cleavable lipid (CH300) or a Tri-chain PEG-ester lipid of the invention (FMM30) combined with peptides K16Y or ME27. Transfections were performed in mouse neuroblastoma cells, Neuro 2A.

Previous results had shown that ME27/ME42 was optimal for Neuro-2A murine neuroblastoma cells. The results presented in FIG. 4 show that the lipids FMM30/DOPE were equally as effective to slightly better at a ratio of 1:4:1 (L:P:D). FMM30/DOPE was again significantly better than the parental lipid combination CH300/DOPE in LPD transfections.

LPD Particle Imaging

Both nanoparticles comprising FMM30 with peptide ME27 at a weight ratio of 0.75:4:1 (L:P:D) shown in FIG. 5 and lipids FMM30/DOPE at the same weight ratio shown in FIG. 6 are quite similar sizes with a combination of shapes including rods and spheres.

As shown in FIG. 7, nanoparticles containing FMM30/DOPE lipids were smaller than those containing FMM30 (no DOPE) across all weight ratios except 0.75:4:1 where both particles were at their smallest at approximately 80 nm.

The invention claimed is:
1. An ionic compound of formula (Ia):

wherein:
each of X and Y are the same or different and is selected from —O—, and —O—C(O)— where the carbonyl carbon is bonded to group $R^1$ or $R^2$;

$R^1$ and $R^2$ are the same or different and are each independently a $C_{12-24}$ hydrocarbyl group which is unsubstituted or substituted by one or more substituents selected from the group consisting of hydroxy, halogen and $OR^4$, wherein $R^A$ is a $C_{1-6}$ hydrocarbyl group;

$R^3$ and $R^4$ are the same or different and are each independently a $C_{1-10}$ hydrocarbyl group which is unsubstituted or substituted by one or more substituents selected from the group consisting of hydroxy, halogen, —OR, —C(O)OH, —CN, —N(R')$_2$, and —C(O)R, wherein each R is the same or different and is a $C_{1-6}$ hydrocarbyl group;

Sp and W are together a bond; or

Sp is a $C_{1-8}$ alkylene group which is unsubstituted or substituted by one or more substituents selected from the group consisting of hydroxy, halogen and OR, wherein R is a $C_{1-6}$ hydrocarbyl group; and W is selected from the group consisting of a bond, —O—C(O)—, —C(O)—O— and —O—; each B is the same or different and is a $C_{1-6}$ alkylene group which is unsubstituted or substituted by one or more substituents selected from the group consisting of hydroxy, halogen, —$OR^A$, —$NR^AR^A$ and —$OC(O)R^A$;

wherein each $R^4$ is independently selected from $C_{1-4}$ hydrocarbyl;

in is an integer from 1 to 8; and

Q is $-OR^5$ or $-O-C(O)-R^5$, wherein $R^5$ is selected from a $C_{12-24}$ hydrocarbyl group which is unsubstituted or substituted by one or more substituents selected from hydroxy, halogen and $OR^4$, wherein $R^4$ is a $C_{1-6}$ hydrocarbyl group.

2. The ionic compound of claim 1 wherein $R^1$ and $R^2$ are the same or different and are each independently a $C_{14-22}$ hydrocarbyl group having one or more double bonds.

3. The ionic compound of claim 1 wherein either Sp and W are both bond, or Sp is an unsubstituted $C_{1-8}$ alkylene group and W is bond, $-C(O)-O-$ or $-O-$.

4. The ionic compound of claim 1 wherein $R^3$ and $R^4$ may be the same or different and each is a straight or branched, unsubstituted $C_{1-4}$ alkyl group.

5. The ionic compound of claim 1 wherein each B is selected from an unsubstituted $C_{1-3}$ alkylene group.

6. The ionic compound of claim 1 wherein m is 1, 2, 3, 4, 5 or 6.

7. The ionic compound of claim 1, wherein $R^1$ and $R^2$ are the same or different and are each independently a $C_{14-22}$ hydrocarbyl group having one double bond; Sp and W are both bond; $R^3$ and $R^4$ are each a straight or branched, unsubstituted $C_{1-4}$ alkyl group; each B is selected from an unsubstituted $C_{1-3}$ alkylene group; m is 2, 3, 4, 5 or 6; and Q is selected from $-OR^5$ and $-O-C(O)-R^5$ and $R^5$ is a $C_{14-22}$ hydrocarbyl group having one double bond.

8. The ionic compound of claim 1 comprising a cation of the formula (Id):

wherein each of $X-R^1$ and $Y-R^2$ and Q is $-O-(CH_2)_8CH[Z]=CH(CH_2)_7CH_3$ or $-O-C(O)-(CH_2)_7CH[Z]=CH(CH_2)_7CH_3$; and m is an integer from 2 to 5.

9. The ionic compound of claim 1, wherein each of $X-R^1$ and $Y-R^2$ are the same and are $-O-(CH_2)_8CH[Z]=CH(CH_2)CH_3$ or $-O-C(O)-(CH_2)_7CH[Z]=CH(CH_2)_7CH_3$, Q is selected from $-O-(CH_2)_8CH[Z]=CH(CH_2)_7CH_3$ or $-O-C(O)-(CH_2)_7CH[Z]=CH(CH_2)_7CH_3$, and m is 3 or 4.

10. A non-viral transfection complex that comprises (i) a ionic compound as defined in claim 1 and a nucleic acid.

11. A non-viral transfection complex of claim 10 that further comprises (iii) a polycationic nucleic acid-binding component and (iv) a cell surface receptor binding component.

12. A pharmaceutical composition which comprises a transfection complex of claim 10 in admixture or conjunction with a pharmaceutically suitable carrier.

13. A vaccine comprising the transfection complex of claim 10.

* * * * *

UNITED STATES PATENT AND TRADEMARK OFFICE
CERTIFICATE OF CORRECTION

| | |
|---|---|
| PATENT NO. | : 11,098,006 B2 |
| APPLICATION NO. | : 16/082785 |
| DATED | : August 24, 2021 |
| INVENTOR(S) | : Helen Claire Hailes et al. |

It is certified that error appears in the above-identified patent and that said Letters Patent is hereby corrected as shown below:

In the Claims

Column 29, Line 3, reading:
- in is an integer from 1 to 8; and -
Should read:
-- m is an integer from 1 to 8; and --;

Column 30, Line 16, reading:
- -O-(CH2)8CH[Z]=CH(CH2)CH3 -
Should read:
-- -O-(CH2)8CH[Z]=CH(CH2)7CH3 --.

Signed and Sealed this
Eighteenth Day of January, 2022

Drew Hirshfeld
*Performing the Functions and Duties of the*
*Under Secretary of Commerce for Intellectual Property and*
*Director of the United States Patent and Trademark Office*